(12) United States Patent
Hanson et al.

(10) Patent No.: US 7,732,225 B2
(45) Date of Patent: Jun. 8, 2010

(54) METHOD FOR MEASURING CONTAMINATION IN LIQUIDS AT PPQ LEVELS

(75) Inventors: Jeffrey Allen Hanson, Allen, TX (US); Lee M. Loewenstein, Dallas, TX (US); Monte Allan Douglas, Richardson, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 11/771,519

(22) Filed: Jun. 29, 2007

(65) Prior Publication Data

US 2008/0121027 A1     May 29, 2008

Related U.S. Application Data

(60) Provisional application No. 60/806,175, filed on Jun. 29, 2006.

(51) Int. Cl.
*H01L 21/00* (2006.01)
*G01N 23/207* (2006.01)

(52) U.S. Cl. .................. 438/14; 257/E21.521; 378/70; 436/178; 134/1.3

(58) Field of Classification Search .................. 438/14; 378/70; 436/178; 134/1.3; 257/E21.521
See application file for complete search history.

(56) References Cited

U.S. PATENT DOCUMENTS

| 5,636,256 | A | * | 6/1997 | Matumura et al. | 378/45 |
| 5,686,314 | A | * | 11/1997 | Miyazaki | 436/177 |
| 5,866,899 | A | * | 2/1999 | Hossain | 250/252.1 |
| 6,077,776 | A | * | 6/2000 | Cho et al. | 438/647 |
| 6,421,414 | B1 | * | 7/2002 | Huber | 378/45 |
| 6,423,148 | B1 | * | 7/2002 | Aoki | 134/3 |
| 6,592,676 | B1 | * | 7/2003 | Mertens et al. | 134/2 |
| 6,937,691 | B2 | * | 8/2005 | Yamagami et al. | 378/45 |
| 7,399,635 | B2 | * | 7/2008 | Hellin et al. | 436/5 |
| 2002/0153482 | A1 | * | 10/2002 | Lin | 250/281 |
| 2005/0162178 | A1 | * | 7/2005 | Steele et al. | 324/755 |
| 2005/0170524 | A1 | * | 8/2005 | Hellin et al. | 436/178 |
| 2005/0276378 | A1 | * | 12/2005 | Ito | 378/70 |

OTHER PUBLICATIONS

Luke Lovejoy, et al., "Assessment of VPD/ICP-MS for Routine Contamination Monitoring in a High-Volume Production Fab" Future Fab International, Issue 13, pp. 140-149.

* cited by examiner

*Primary Examiner*—W. David Coleman
(74) *Attorney, Agent, or Firm*—John J. Patti; Wade J. Brady, III; Frederick J. Telecky, Jr.

(57) ABSTRACT

A method of manufacturing a semiconductor device includes placing a sample of a liquid chemical containing a contaminant on a substantially impurity-free surface of a substrate. The liquid chemical is evaporated, leaving the contaminant on the surface. The contaminant is concentrated in a scanning solution, which is then evaporated to form a residue. A concentration of the contaminant in the residue is determined.

6 Claims, 4 Drawing Sheets

METHOD FOR MEASURING CONTAMINATION IN LIQUIDS AT PPQ LEVELS

CROSS-REFERENCE TO PROVISIONAL APPLICATION

This application claims the benefit of U.S. Provisional Application No. 60/806,175 entitled "Method for Measuring Metals in Ultrapure Water at PPQ Levels" to Jeffrey Allen Hanson, et al., filed on Jun. 29, 2006 which is commonly assigned with the present invention and incorporated herein by reference as if reproduced herein in its entirety.

TECHNICAL FIELD

The embodiments discussed herein are directed to detection of contamination in liquids, and more specifically, to detection thereof in liquid chemicals used in semiconductor device manufacturing.

BACKGROUND

Some manufacturers rely on extremely pure chemicals in the manufacturing process. Many such chemicals are used in liquid form, and may be provided by a chemical manufacturer with a specified level of purity. In some cases, such as semiconductor-grade water, such liquids are generated in a pure form on-site by a semiconductor manufacturer. Of particular concern in the semiconductor context are metal ion contaminants, particularly sodium that can poison semiconductor devices by causing a shift of transistor threshold voltage to the point that a semiconductor device becomes nonfunctional. In high enough concentration, such contaminants may reduce product yield, while in lower concentration the contaminant may reduce long-term reliability of the device.

Manufacturers often determine the level of impurities in the liquid chemicals used. A common protocol is to provide a sample to a service provider who characterizes the species and concentration of impurities and provides a report of the results. A common technique used to characterize the level of impurities in the sample is inductively-coupled plasma mass spectrometry (ICP-MS). While characterization using ICP-MS generally can measure impurity concentrations as low as parts-per-trillion (PPT), in some cases the manufacturer may require even lower levels of contamination.

Furthermore, the service provider is generally not co-located with the manufacturing facility, so the sample may be transported by courier in a container to the provider location. Such transportation inherently risks contamination from the container, the courier, or handling by the provider. Some manufacturers, such as semiconductor manufacturers, operate facilities such as clean rooms, in which contamination is minimized by stringent protocols. In such cases, it may be counterproductive to transport a sample of a liquid outside of the facility to another site for analysis, thereby risking contamination.

What is needed is a method of characterizing contamination of water that overcomes the limitations of currently existing methods.

SUMMARY

There is provided, in one embodiment, a method of manufacturing a semiconductor device. The method includes placing a sample of a liquid chemical containing a contaminant on a substantially impurity-free surface of a substrate. The liquid chemical is evaporated, leaving the contaminant on the surface. The contaminant is concentrated in a scanning solution, which is evaporated to form a residue. A concentration of the contaminant in the residue is then determined.

Another embodiment is a method of manufacturing a semiconductor device. A surface of a silicon wafer is exposed to hydrogen fluoride gas a first time, and then scanned with a cleaning solution to concentrate an impurity therein. The cleaning solution is discarded. A layer of water containing a metal contaminant is formed covering substantially the entire surface. The water is evaporated to leave the contaminant on the surface. The surface is exposed to hydrogen fluoride gas a second time, and then scanned with a scanning solution to concentrate the contaminant therein. The scanning solution is evaporated to leave the contaminant on the surface. A concentration of the contaminant on the surface is determined using a surface analytic technique.

Another embodiment is a method of determining a contamination level in a liquid chemical. A sample of the liquid chemical including a contaminant is placed on a substantially impurity-free surface of a substrate having a surface area. The liquid is evaporated to leave the contaminant on the surface. The contaminant is concentrated in an area smaller than the surface area, and a concentration of the contaminant is determined in at least a portion of the smaller area.

BRIEF DESCRIPTION OF THE DRAWINGS

Reference is now made to the following descriptions taken in conjunction with the accompanying drawings, in which.

DETAILED DESCRIPTION

The sensitivity of prior art characterization methods is limited by the detection limits of the characterization tool, by the accuracy of calibration standards, and by incidental contamination of a sample transported to the tool. Of particular concern in semiconductor manufacturing are metal ions such as, e.g., $Na^+$ and $K^+$. Such ions may be relatively mobile in a completed integrated circuit device. Under some conditions, mobile metal ions may migrate to the gate oxide of MOSFETs and cause a detrimental shift of threshold voltage. In some cases, an ultrapure water supply may become contaminated with metal ions, which may result in loss of product yield or premature failure. In other cases, a contaminated source of a liquid chemical such as a solvent or photoresist is contaminated, and the contamination is transferred to the product during use of the chemical. In some situations, product yield may be impacted by contamination that is below the threshold of detection by common characterization methods, such as ICP-MS, making the yield of a semiconductor device a more accurate measure of the purity of a liquid chemical.

With the invention, it has been realized that semiconductor characterization tools designed to characterize atomic species present on the surface of a substrate may be used to determine the presence and concentration of a contaminant in a liquid chemical sample. In various embodiments described below, the liquid chemical is used to intentionally contaminate the surface of a substrate. The contaminant is concentrated into a small region of the substrate, increasing the sensitivity of later characterization. Quantitative characterization of an amount of the contaminant in a sample area can be performed using a trace element surface analytical tool. The concentration of the contaminant in the liquid chemical sample may then be determined from the characterization data. Corrective action may be taken if necessary to reduce the concentration of the contaminant in the liquid chemical supply.

Figure 1:
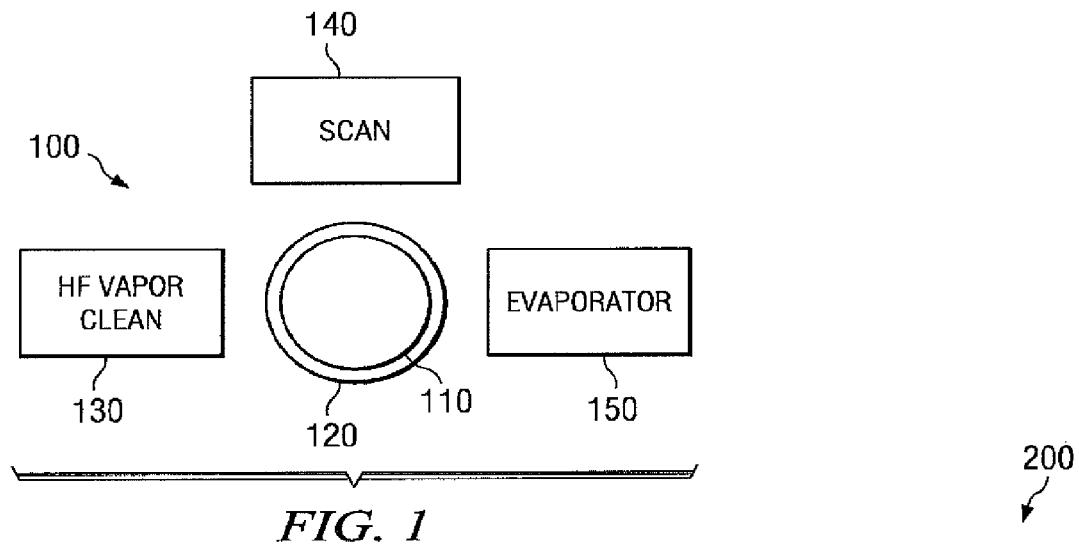
FIG. 1 illustrates a VPD-DC tool.

FIG. 1 is a schematic illustration of a vapor phase decomposition-droplet collection (VPD-DC) tool 100 suitable for use in the embodiments described herein. VPD-DC is a method by which trace impurities on the surface of a semiconductor substrate are collected into a liquid sample. A non-limiting example of a VPD-DC tool designed for use in a semiconductor manufacturing environment is the WSPS tool manufactured by GeMeTec U.S.A., Inc., located in Dallas, Tex. Embodiments below recognize the utility of practicing the invention with ultrapure water in a semiconductor manufacturing context, but the invention is not so limited. For example, the invention, as exemplified by the embodiments discussed herein, could be used to determine the level of contaminants in a liquid chemical of any purity for purposes wholly unrelated to semiconductor manufacturing processes.

In semiconductor applications, the VPD-DC tool is provided as a means to characterize contamination on the surface of a semiconductor substrate. In the embodiments described herein, contamination is intentionally added to and concentrated on the substrate using VPD-DC. Intentionally contaminating the substrate is contrary to conventional use of VPD-DC and to the conventional wisdom of semiconductor processing, in which substrates are carefully protected from contamination.

As used herein, a liquid chemical is any substance in a liquid phase that is compatible with the VPD-DC technique. In one aspect, the liquid chemical is capable of substantially complete evaporation, such that any contamination therein is left on the substrate surface. In some cases, the chemical has a liquid phase at room temperature and pressure (RTP), about 25° C. and 100 kPa. In some cases, where the vapor pressure of the liquid is less than about 30 kPa at room temperature, elevated temperature, reduced pressure, or both may be used to accelerate evaporation. In other cases, where the vapor pressure at room temperature is greater than about 100 kPa, the liquid chemical and the substrate may be cooled or placed under pressure to reduce the rate of evaporation where desirable to make the evaporation process more controllable. In some cases, venting of the vapor may be required when the liquid chemical is toxic. Means to provide appropriate temperature, pressure, and venting are conventional and within the ability of those skilled in the relevant arts.

Examples of such substances include, without limitation, water, organic solvents, aqueous acidic solutions, oils, and the liquid phase of substances that could be a gas at RTP. In the context of semiconductor manufacturing, such substances further include ultrapure water, isopropanol, cleaning bath solvents, and photoresist solvents.

The VPD-DC method typically includes exposing the substrate to hydrogen fluoride (HF) gas and water vapor, referred to herein as a fuming process. In some cases, the HF and water vapor are generated by bubbling $N_2$ gas through a hydrofluoric acid solution. In other cases the partial pressures of the HF and $H_2O$ may be precisely controlled to achieve a desired degree of reaction on the surface of the substrate. A stage on which the substrate rests may be cooled to promote condensation of an $HF/H_2O$ film onto the substrate. The film may then decompose any native oxide on the surface and dissolve any impurities on the surface. When the substrate is a semiconductor wafer, the surface typically becomes hydrophobic when the native oxide is removed, at which point the film beads on the surface. The beads may then be collected in a water droplet scanned over the surface to collect and concentrate any impurities in the droplet. In some cases, the droplet may be retained for later analysis, while in others the droplet is left on the substrate and dried.

In FIG. 1, a substrate 110 rests on a wafer handling stage 120. The wafer may be transported to chambers 130, 140 and 150 as desired. A fuming chamber 130 provides the HF vapor clean process. A scanning chamber 140 provides the fluid dispense and scanning process. An evaporation chamber 150 provides for evaporation of water on the substrate 110 surface using heat, vacuum or both. When necessary to control the evaporation rate of the liquid, the evaporation chamber may also provide cooling or pressure.

Figure 2:
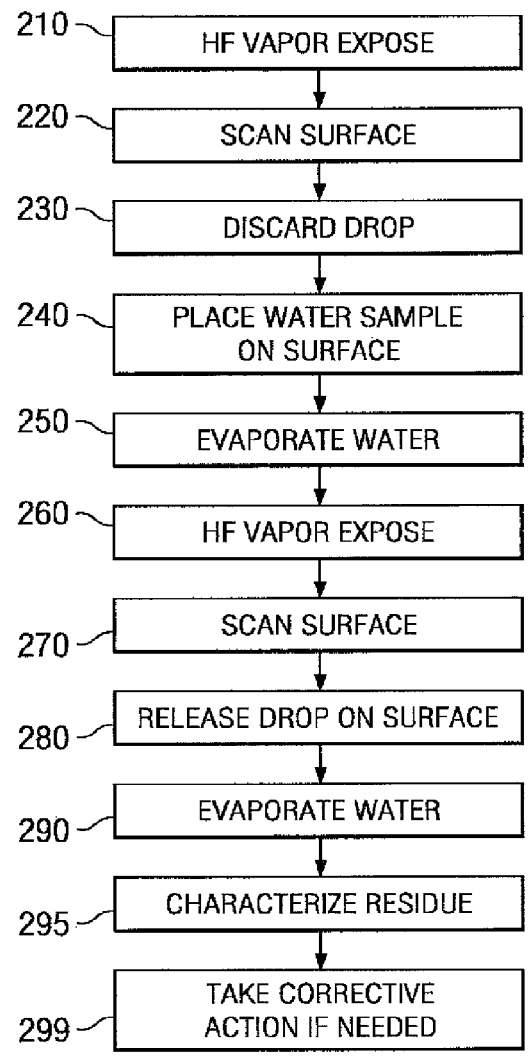
FIG. 2 illustrates a method.

FIG. 2 illustrates an embodiment of a method 200 according to the invention. In steps 210-230 the substrate 110 may be optionally cleaned. The substrate 110 may be, e.g., a silicon wafer or another semiconductor material or a high-purity polymer. The substrate 110 in general includes an initial impurity on a surface thereof. Such impurity may have been acquired from shipping, storage or handling, and may include, e.g., organic or ionic chemical species. At sufficient concentration, the initial impurity may obscure a contamination signal due to contaminant of interest in an ultrapure water sample to be characterized. In such cases, the surface of the substrate 110 is cleaned. In some cases, however, the substrate 110 may begin the method in a clean or known state, making cleaning unnecessary. In other cases, the surface of the substrate 110 may be prepared in a manner which results in a clean substrate, such as by cleaving.

When the substrate is cleaned, any cleaning method that results in a substrate 110 surface substantially free of impurity and oxide may be used. The surface is substantially free of impurity when any contaminants are at or below detection limits of methods typically used to characterize the contamination level of a substrate surface, such as, e.g., total reflection x-ray fluorescence (TRXRF) spectroscopy. The cleaning may be performed in any location, and may be performed by, e.g., a manufacturer or vendor of the substrate 110, or by the semiconductor manufacturer in a manufacturing environment. As used herein, impurities are trace elements not included in the substrate 110. For example, if the substrate 110 is a silicon wafer, any dopants in the wafer are not considered impurities, but any metal ions, some non-metal anions or organic molecules are so considered. A metal is any element except a nonmetal. A nonmetal is an element of the group, Hydrogen, Boron, Carbon, Silicon, Nitrogen, Phosphorus, Oxygen, Sulfur, Selenium, Tellurium, Fluorine, Chlorine, Bromine, Iodine, Astatine, Helium, Neon, Argon, Krypton, Xenon, and Radon. Non-metal anions of interest may include halogens and sulphur.

The method 200 illustrates without limitation an embodiment in which the substrate 110 is cleaned using the VPD-DP method. While the discussion of the method 200 refers to the VPD-DC tool 100, other tool configurations that provide the processes described herein may be used without departing from the scope of the invention. In a step 210, the substrate 110 is exposed to HF gas and water vapor. When the WSPS tool is used, fuming process conditions include a substrate temperature of about 12° C. and a nitrogen ambient at a pressure of about 77 kPa. Nitrogen may be flowed at a rate of about 80 L/min through a 49% hydrofluoric acid solution. At least some of any impurities present on the substrate 110 surface are dissolved in an aqueous layer of hydrofluoric acid formed thereon, which then beads as described previously. In a step 220, the substrate 110 is transported to the scanning chamber 140. The substrate 110 is scanned, as described below, to collect the aqueous layer and concentrate any impurities dissolved therein.

Figure 3:
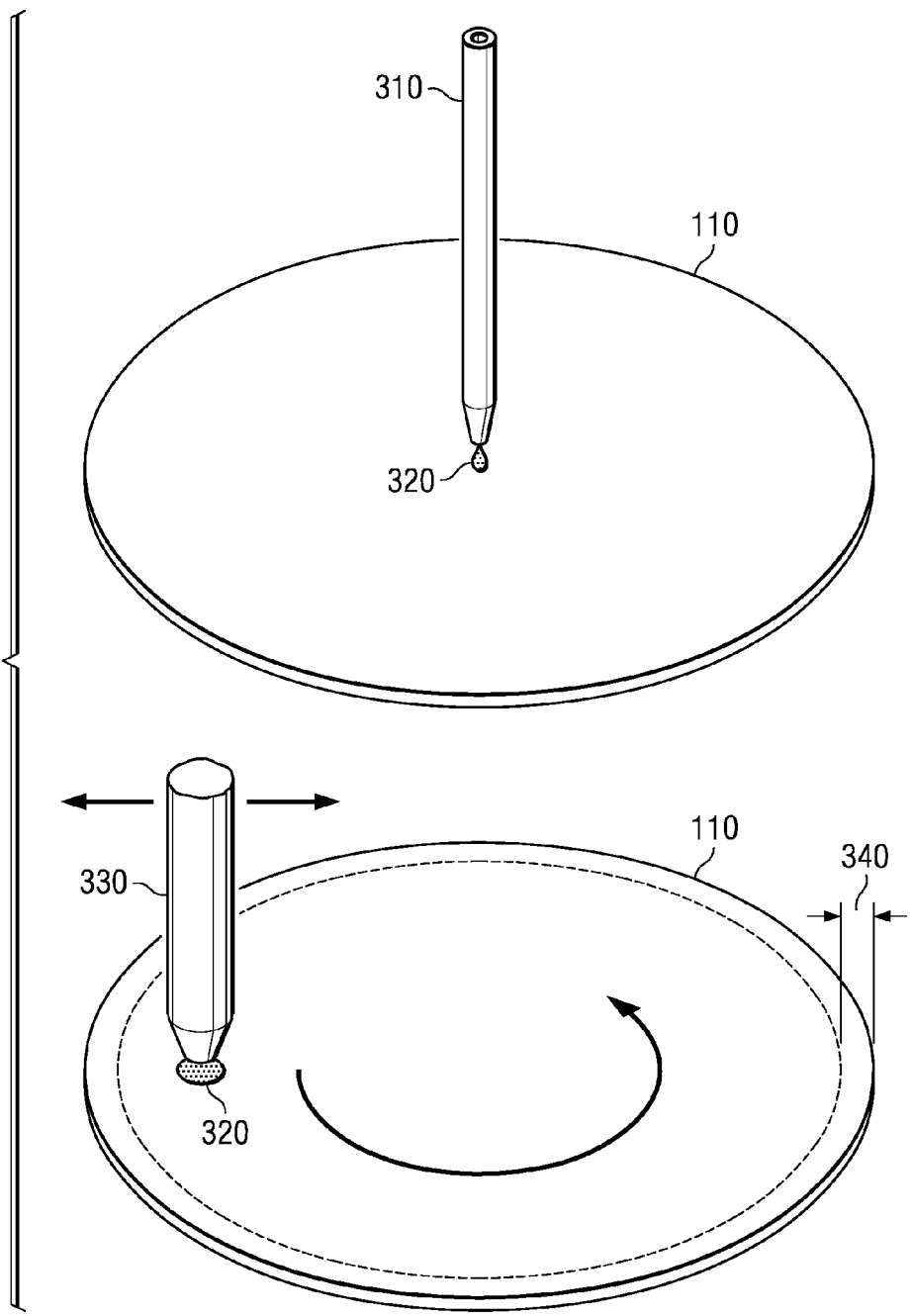
FIGS. 3-5 illustrate aspects of the method.

FIG. 3 conceptually illustrates the scanning process. A pipette 310 deposits a droplet 320 of a scanning solution. The volume of the droplet 320 may be varied to adjust the diameter thereof when resting on the substrate 110. In a nonlimiting example, a volume is about 120 μL to about 150 μL results in a diameter of about 3 mm. The scanning solution may be an aqueous solution including one or more additives to promote dissolving of impurities into the scanning solution. Typically, this scanning solution can be comprised of an aqueous solution of nitric acid and hydrogen peroxide or an aqueous solution of hydrofluoric acid and hydrogen peroxide. This aspect is discussed in greater detail below. A scanning tip 330 may then secure the droplet 320 by vacuum. For example, the substrate 110 may then be rotated while the scanning tip 330 is translated along the radius of the substrate 110. The scanning tip 330 may be translated one or more times to the edge of the substrate, minus an exclusion zone 340, to collect the aqueous layer. In a step 230, the droplet is discarded, disposing of the collected impurities. At this point, the substrate 110 surface is considered clean. If the substrate 110 is a silicon wafer, the surface is also hydrophobic by virtue of having removed any oxide on the surface in the fuming process. When the substrate 110 is a high-purity polymer, the surface may be intrinsically hydrophobic.

Figure 4:
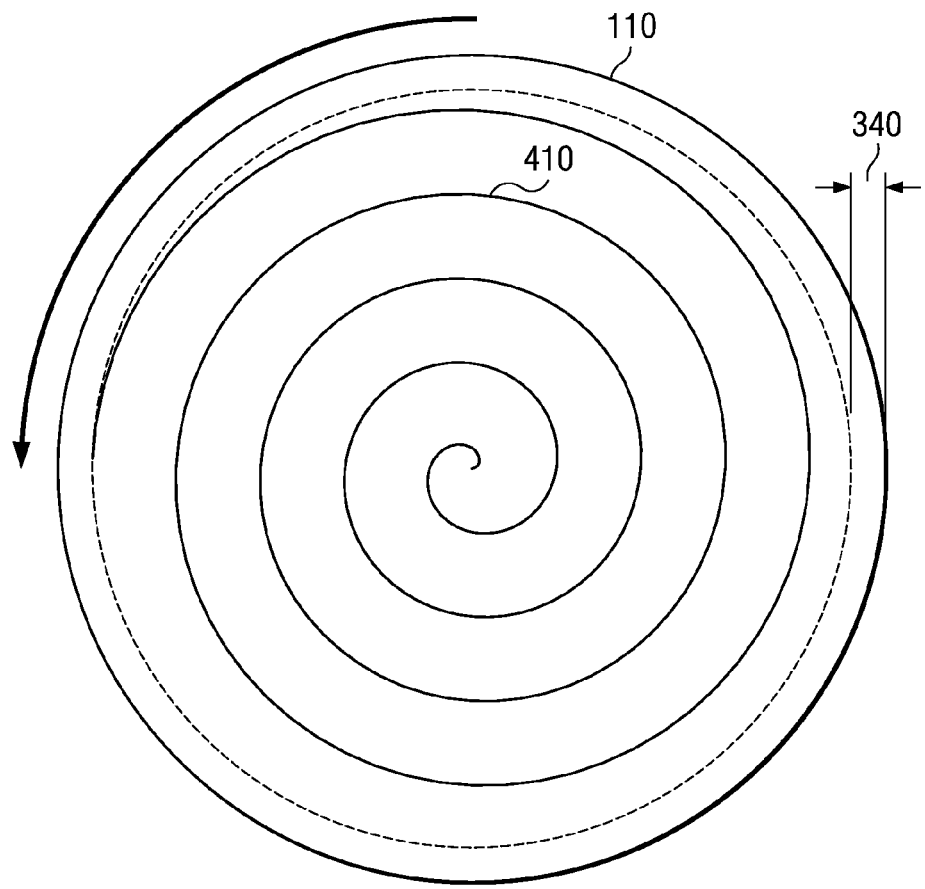

FIG. 4 conceptually illustrates a path 410 that the droplet 320 traces over the substrate 110. The combination of translation of the scanning tip 330 and rotation of the substrate 110 results in a spiral. The rate of translation and rotation may be set to result in complete coverage of the substrate 110 by the droplet 320 in a single translation of the scanning tip 330 from the center of the substrate 110 to the edge and back, with the exception of the exclusion zone 340.

In a step 240 a sample of a liquid chemical is placed on the substrate 110. While the illustrated embodiment describes use of the method to characterize ultrapure water, any liquid chemical as previously described is within the scope of the invention. Ultrapure water means water that is substantially free of dissolved ionic and organic contaminants. Contaminants are any species other than $H_2O$, $H_3O^+$ or $OH^-$. Water is substantially free of contaminants when any contaminants are at or below detection limits of methods typically used to characterize the contamination level of ultrapure water, such as, e.g., ICP-MS. Detection limits of ICP-MS are typically on the order of parts per trillion (PPT). In one aspect, ultrapure water is suitable for semiconductor manufacturing operations. In another aspect, ultrapure water has a resistivity of at least about 18 MΩ-cm. While being substantially free of contaminants, ultrapure water may include contaminants at a sufficient concentration to result in decreased yield of semiconductor devices when used in manufacturing operations.

Figure 5:
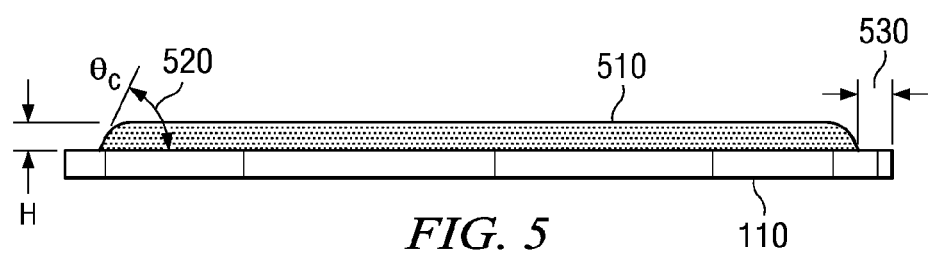

FIG. 5 illustrates the substrate 110 with a sample 510 placed thereon. The water may be placed, e.g. using a pipette or similar device. In general, a liquid on a surface will form a contact angle 520, $\theta_c$. A liquid chemical with a low contact angle wets the surface, whereas a liquid with a high contact angle is non-wetting. For example, water forms a contact angle of about 20° or less on a silicon dioxide surface, therefore wetting the surface and tending to spread. Such a surface is considered hydrophilic. But water on an oxide-free silicon surface forms a contact angle of 45° or greater and therefore is non-wetting, causing the water to bead. In this case, the surface is considered hydrophobic.

When the liquid chemical is water, or an aqueous solution, a hydrophobic surface of the substrate 110 enables a puddle of water to form on the substrate 110, with a height H, covering substantially all of the substrate 110. This aspect also applies in general when the liquid chemical is not water, when the liquid does not wet the substrate 110. The substrate 110 has a surface area that may be considered to be substantially coextensive with the upper horizontal surface of the substrate 110 as illustrated in FIG. 5. The volume of the sample 510 may be as much as the surface area of the substrate 110 times the height. In some cases, a 200 mm silicon wafer may hold, e.g., about 20 mL of water. In practice, an edge allowance 530 of 3-5 mm is desirable to reduce the chance of spilling the sample 510 when the wafer is moved.

In a step 250, the sample 510 is evaporated in, e.g., the evaporation chamber 150. The evaporation process may include heating the sample 510, reducing the ambient pressure in the evaporation chamber 150, or both. In an embodiment in which the liquid chemical is water, a temperature of about 50° C. may be used at a pressure of about 1.3 kPa. In one aspect of the evaporation process, any contamination added thereby is below the detection limit of the characterization method used to determine a concentration of contamination on the substrate 110 at a later step.

Where the liquid chemical has a contact angle less than about 45°, e.g., does not bead on the substrate 110 surface, a smaller volume of the liquid chemical may be placed on the substrate 110 in the step 240. In this case, it may be desirable to repeat steps 240 and 250 as many times as desired to result in a sufficient level of contamination to be detectable in a later step of the method 200.

In one aspect of the step 250, the water is completely evaporated to form a contaminant residue on the surface. Completely evaporated means that a total volume of any remaining water on the surface is an insignificant fraction, e.g., less that 10% of a scanning droplet used in a second scanning step as described below. Preferably, the volume of any remaining water on the surface is less than 5% of the scanning droplet volume. More preferably, the volume of the remaining water is less than 1% of the scanning droplet volume.

Figure 6:
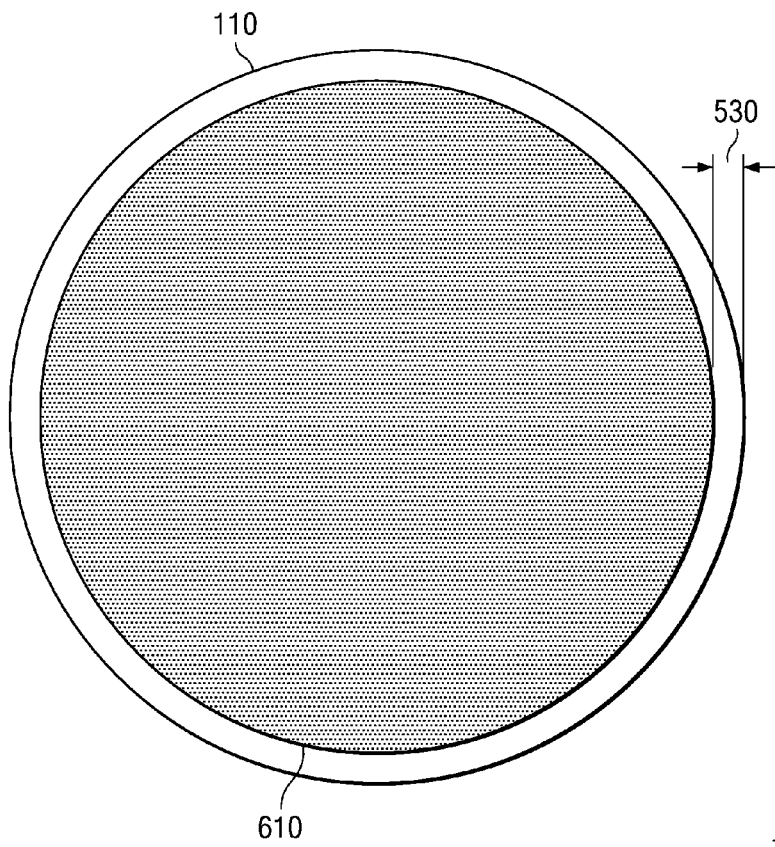
FIGS. 6 and 7 illustrate a substrate with contamination.

The residue is thought to be distributed substantially homogeneously, excepting the edge allowance 530, as a contaminated region 610 as illustrated in FIG. 6. Exposure of the substrate 110 surface to air and water is also thought to result in a thin native oxide formed thereon. A contaminant in the residue may be associated with the oxide layer. Such association may be relatively weak, such as by van der Waals forces, or relatively strong, such as by chemical bonding or solid solution.

In some cases, the residue contains a contaminant that was present in the sample 510 in ionic form, including any metal ions. In other cases, the residue may include non-metal anions of interest, such as $Cl^-$ and $Br^-$. In still other cases, the residue may include an organic contaminant. However, it is thought that some organic contaminants are sufficiently volatile that a concentration of these organic contaminants in the residue may not accurately reflect the concentration of the organic contaminant in the sample 510. In such cases, calibration standards for such organic contaminants may be required where greater accuracy is needed.

As described previously with respect the steps 210-230, the substrate 110 is again treated using the VPD-DC method in steps 260, 270, 280. In the step 260, the substrate 110 may be moved to the fuming chamber 130 and exposed to $HF/H_2O$ vapor. It is thought that any native oxide formed on the substrate 110 surface after the steps 240, 250 is removed by the HF. A contaminant that is associated with the oxide or the surface is then thought to enter solution in beads formed on the substrate 110 surface when the oxide is removed.

In a step 270, the substrate 110 surface is again scanned using a scanning solution as described with respect to the step 220. The scanning solution in the step 270 may be the same scanning solution used in the step 220, but need not be. The scanning causes the contaminants to be concentrated in the droplet 320. In one aspect, the scanning solution is designed to dissolve the contaminant therein.

In one aspect, the scanning solution is a polar solvent. In some cases the scanning solution does not wet the substrate 110 surface. In another aspect, a solubility of a metal ion of interest is sufficient to dissolve the contaminant in the contaminated region 610. In some embodiments, the scanning solution may be water or an aqueous solution. In other embodiments, the scanning solution may be a non-aqueous polar solvent, such as, e.g., dimethyl sulphoxide (DMSO). In some cases, the scanning solution can form a contact angle with the substrate 110 less than about 45°. This situation may occur, e.g., when substrate 110 is other than a semiconductor substrate or the when the scanning solution is non-aqueous. In such cases, the rate of rotation of the substrate 110 during scanning may be determined that ensures that the droplet 320 remains intact during scanning.

The scanning solution may include additives to increase or reduce the pH thereof, or to promote oxidation of a metal contaminant, e.g. Oxidation refers to increasing the oxidation state of a metal by removing an electron therefrom. In one embodiment, the scanning solution includes an acid such as nitric acid, hydrochloric acid, or hydrofluoric acid to reduce the pH below neutral. In another embodiment, the scanning solution includes a peroxide such as hydrogen peroxide or persulfuric acid as an oxidizing agent. In some cases, the scanning solution includes both an acid and a peroxide. In one embodiment, the scanning solution includes about 1-2% w/w nitric acid and about 1-2% w/w hydrogen peroxide in water. In other embodiments, the scanning solution may include more than 5% hydrogen peroxide. In some cases, the scanning solution may include up to about 75% hydrogen peroxide.

In the step 280, the droplet 320 is not discarded as it was in the step 230. The droplet 320 may optionally be placed in a container and transported to a characterization facility to determine a concentration of a contaminant therein using a technique such as ICP-MS or graphite furnace atomic absorption spectrometry (GFAAS). This embodiment advantageously allows the substrate 110 to be reused, thereby reducing costs. Alternatively, the droplet 320 may be left on the substrate 110. In one embodiment, the droplet 320 is left in the center of the substrate 110 to provide a known location for later analysis.

Figure 7:
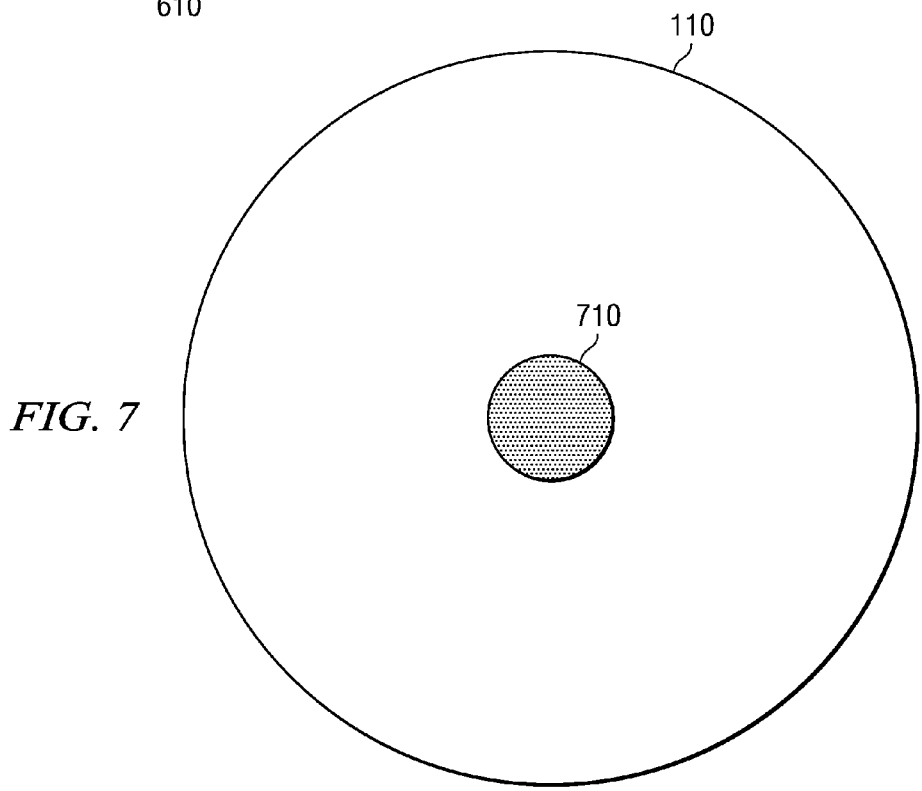

In a step 290, the substrate 110 may be transferred to the evaporation chamber 150. The droplet 320 may be evaporated using elevated temperature, reduced pressure, or both as previously described. The evaporation results in a residue 710 concentrated at the center of the substrate 110, as illustrated in FIG. 7. In a step 295, the substrate 110 is then transported to a characterization tool for analysis in a manner designed to prevent contamination of the residue 710.

The concentration of the contaminant into a small spot at the center of the substrate has the advantageous effect of increasing the sensitivity of a characterization method used to quantify the concentration of the contaminant in the ultrapure water supply. In a non-limiting example, when the substrate 110 has a radius of 150 mm, and the droplet 320 has a radius of 3 mm, a contaminant may be concentrated by more than three orders of magnitude in the residue 710. Thus, in some cases a contaminant that would otherwise have a concentration below the detection limit of the characterization method may become detectable by the concentrating at the center of the substrate 110.

One characterization method that may be used in the step 295 is time-of-flight secondary-ion-mass-spectrometry (TOF-SIMS). TOF-SIMS is a highly sensitive method of trace elemental and molecular surface analysis. The method may be used to determine a concentration of an ionic species in the residue 710, and in some cases may be able to identify organic contaminants as well. However, TOF-SIMS typically uses a spot size of ranging from about 40 $\mu m^2$ to about 500 $\mu m^2$ so is generally used to determine a quantity of a contaminant in a portion of the residue 710. Another method that can be employed is TRXRF.

The measured quantity of contamination in the sample spot may be used directly, or may be converted to a concentration in the sample 510. Direct use may include, e.g., comparing the measured value to historical values to detect contamination excursions in a source of water. Optionally, a quantitative concentration of the contaminant may be determined by using calibration data.

In a nonlimiting example, calibration may include providing a water sample with a known concentration of a known contaminant and concentrating the contaminant at the center of a substrate as described in the method 200. In some cases, calibration standards may be prepared using more than one known concentration of the contaminant. The known concentration of the known contaminant in the water samples may optionally be characterized by a method such as ICP-MS to provide measured concentration values. The water samples may then be characterized as described herein using TOF-SIMS to determine an areal concentration (atoms/$cm^2$) of the contaminant.

The areal concentrations and the known or measured concentrations of the calibration standards may be graphically or numerically correlated to determine a relationship between the areal concentrations and the known concentrations. This relationship may then be extrapolated to determine an unknown concentration of a contaminant in a water sample. In some cases, the extrapolated concentration may be below the ICP-MS detection limits of that contaminant. In some cases, the relationship may be extrapolated to the detection limit of the TOF-SIMS or other surface analytic method.

Another characterization method that may be used is TRXRF spectroscopy. In this method, a residue sample on a substrate surface may be illuminated by an x-ray beam, and elements therein identified by their characteristic x-ray fluorescence spectra. In general, TRXRF has higher detection limits than TOF-SIMS, and is not suited to identify molecular species or low atomic weight species on silicon. However, TRXRF provides two advantages of particular relevance.

First, the analysis spot size may be large enough, e.g. about 1 $cm^2$, to include the entire area occupied by the residue 710, thus including substantially the entire residue. Thus, with knowledge of the volume of the sample 510, the concentration of a contaminant therein may be directly determined. Second, TRXRF tools have been developed for use in semiconductor fabrication facilities. Thus, a substrate 110 prepared as described in the method 200 may be transferred directly from the VPD-DC tool 100 to a TRXRF tool for analysis. This reduces the chance of undesired contamination and provides for faster results. When desired, TRXRF data may be calibrated using the method described with respect to TOF-SIMS.

TOF-SIMS or TRXRF characterization of the residue 710 as described herein advantageously provides sensitivity to a contaminant in the sample 510 at the parts-per-quadrillion (PPQ) level or better, which in some cases is an improvement of at about three orders of magnitude or more over the ICP-MS method. Other advantages include characterization without removing the sample 510 from the fabrication environment, and use of wafer-based characterization tools already installed in a semiconductor manufacturing facility for other purposes such as failure analysis. Moreover, the embodiments described herein may reduce the exposure of the manufacturer to risk that a third party provider of characterization services is unable to meet the schedule requirements of the manufacturer, reducing down time and related expenses.

In a step 299, a level of contamination in a liquid chemical supply may be reduced in response to the characterization of the concentration of a contaminant therein. The reduction may result, e.g., from determining and removing a source of the contaminant, or performing periodic maintenance on a system supplying ultrapure water, or obtaining a liquid chemical of higher purity from a chemical supplier. A manufacturing process using the liquid chemical may then be performed after the level of contamination is reduced, resulting in lower risk of contamination-related yield loss.

Those skilled in the art will appreciate that other and further additions, deletions, substitutions and modifications may be made to the described embodiments without departing from the scope the disclosure set forth herein.

What is claimed is:

1. A method for measuring contamination of ultrapure water (UPW), the method comprising:
    cleaning a silicon wafer;
    exposing the silicon wafer to hydrogen fluoride vapor;
    placing a volume of the UPW onto the silicon wafer;
    drying the UPW on the silicon wafer; and
    measuring metallic contaminants remaining on the silicon wafer from the UPW.

2. The method of claim 1, wherein silicon wafer is about 200 mm and the volume of UPW is about 200 ml.

3. The method of claim 1, wherein the step of measuring further comprises:
    exposing the silicon wafer having the metallic contaminants remaining from the UPW to hydrogen fluoride vapor;
    scanning the silicon wafer with a solution to collect the metallic contaminants; and
    analyzing the solution to determine the concentration of the metallic contaminants in the UPW.

4. The method of claim 1, wherein the step of measuring further comprises measuring metallic contaminants on the silicon wafer using total reflection x-ray fluorescence (TRXRF) or time-of-flight secondary-ion-mass-spectrometry (TOF-SIMS).

5. The method of claim 3, wherein the solution is an aqueous solution of nitric acid and hydrogen peroxide or an aqueous solution of hydrofluoric acid and hydrogen peroxide.

6. The method of claim 5, wherein the step of analyzing further comprises analyzing the solution with an inductively coupled plasma mass spectrometry (ICP-MS) or graphite furnace atomic absorption spectrometry (GFAAS).

* * * * *